US007135167B2

(12) United States Patent
Legrand et al.

(10) Patent No.: US 7,135,167 B2
(45) Date of Patent: *Nov. 14, 2006

(54) OXIDIZING COMPOSITION FOR TREATING KERATIN FIBERS, COMPRISING A PARTICULAR AMINOSILICONE

(75) Inventors: Frédéric Legrand, Courbevoie (FR); Jean-Marie Millequant, Saint-Maur des Fosses (FR)

(73) Assignee: L'Oreal, SA, Paris (FR)

( * ) Notice: Subject to any disclaimer, the term of this patent is extended or adjusted under 35 U.S.C. 154(b) by 554 days.

This patent is subject to a terminal disclaimer.

(21) Appl. No.: 10/290,372

(22) Filed: Nov. 8, 2002

(65) Prior Publication Data
US 2003/0152543 A1    Aug. 14, 2003

(30) Foreign Application Priority Data
Nov. 8, 2001  (FR)  ................................... 01 14474

(51) Int. Cl.
*A61Q 5/10* (2006.01)
*A61Q 5/08* (2006.01)

(52) U.S. Cl. ............................... 424/70.122; 424/70.6; 424/62

(58) Field of Classification Search .................... None
See application file for complete search history.

(56) References Cited

U.S. PATENT DOCUMENTS

| | | | |
|---|---|---|---|
| 2,047,398 A | 7/1936 | Voss et al. |
| 2,261,002 A | 10/1941 | Ritter |
| 2,271,378 A | 1/1942 | Searie |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,578 A | 6/1971 | Kamphausen |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |
| 4,165,367 A | 8/1979 | Chakrabarti |
| 4,172,887 A | 10/1979 | Vanlerberghe et al. |
| 4,217,914 A | 8/1980 | Jacquet et al. |
| 4,223,009 A | 9/1980 | Chakrabarti |
| 4,237,243 A | 12/1980 | Quack et al. |
| 4,277,581 A | 7/1981 | Vanlerberghe et al. |
| 4,282,203 A | 8/1981 | Jacquet et al. |
| 4,349,532 A | 9/1982 | Vanlerberghe et al. |
| 4,509,949 A | 4/1985 | Huang et al. |
| 4,591,610 A | 5/1986 | Grollier |
| 4,608,250 A | 8/1986 | Jacquet et al. |
| 4,673,568 A | 6/1987 | Grollier et al. |
| 4,693,935 A | 9/1987 | Mazurek |
| 4,702,906 A | 10/1987 | Jacquet et al. |

(Continued)

FOREIGN PATENT DOCUMENTS

AU     200039428     2/2001

(Continued)

OTHER PUBLICATIONS

"Encyclopedia of Chemical Technology", Kirk-Othmer, Third Edition, 1982, vol. 15, pp. 439-458.

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

The disclosure relates to a cosmetic composition for treating keratin fibres, such as hair, comprising, in a cosmetically acceptable medium: (i) at least one oxidizing agent; and (ii) at least one aminosilicone.

The disclosure further relates to the composition's uses, such as dyeing, bleaching, and permanently reshaping keratin fibres.

The disclosure also relates to the processes and devices for bleaching, dyeing or permanently reshaping human keratin fibres using the composition.

59 Claims, No Drawings

U.S. PATENT DOCUMENTS

| | | | |
|---|---|---|---|
| 4,710,314 A | 12/1987 | Madrange et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,770,873 A | 9/1988 | Wolfram et al. | |
| 4,839,166 A | 6/1989 | Grollier et al. | |
| 4,957,732 A | 9/1990 | Grollier et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,061,289 A | 10/1991 | Clausen et al. | |
| 5,077,040 A | 12/1991 | Bergmann et al. | |
| 5,085,860 A | 2/1992 | Junino et al. | |
| 5,089,252 A | 2/1992 | Grollier et al. | |
| 5,106,612 A | 4/1992 | Maignan et al. | |
| 5,139,037 A | 8/1992 | Grollier et al. | |
| 5,154,918 A | 10/1992 | Maignan et al. | |
| 5,196,189 A | 3/1993 | Jacquet et al. | |
| 5,210,324 A | 5/1993 | Farrar et al. | |
| 5,340,367 A | 8/1994 | Schultz et al. | |
| 5,344,464 A | 9/1994 | Madrange et al. | |
| 5,380,340 A | 1/1995 | Neunhoeffer et al. | |
| 5,466,878 A | 11/1995 | Junino et al. | |
| 5,534,267 A | 7/1996 | Neunhoeffer et al. | |
| 5,538,717 A | 7/1996 | De La Poterie | |
| 5,583,257 A | 12/1996 | Junino et al. | |
| 5,626,840 A | 5/1997 | Thomaides et al. | |
| 5,663,366 A | 9/1997 | Neunhoeffer et al. | |
| 5,708,151 A | 1/1998 | Mockli | |
| 5,741,337 A | 4/1998 | Bone et al. | |
| 5,756,076 A | 5/1998 | Cervantes et al. | |
| 5,766,576 A | 6/1998 | Lowe et al. | |
| 5,773,611 A | 6/1998 | Zysman et al. | |
| 5,833,997 A | 11/1998 | Mahieu et al. | |
| 5,925,341 A | 7/1999 | Cervantes et al. | |
| 5,958,392 A | 9/1999 | Grollier et al. | |
| 5,976,195 A | 11/1999 | De La Mettrie et al. | |
| 6,010,541 A | 1/2000 | De La Mettrie et al. | |
| 6,071,504 A | 6/2000 | Kawai et al. | |
| 6,099,592 A | 8/2000 | Vidal et al. | |
| 6,099,593 A | 8/2000 | Terranova et al. | |
| 6,143,286 A * | 11/2000 | Bhambhani et al. | 424/70.1 |
| 6,177,090 B1 | 1/2001 | Dubief et al. | |
| 6,179,881 B1 | 1/2001 | Henrion et al. | |
| 6,214,326 B1 | 4/2001 | Dupuis | |
| 6,254,646 B1 | 7/2001 | De La Mettrie et al. | |
| 6,260,556 B1 | 7/2001 | Legrand et al. | |
| 6,284,003 B1 | 9/2001 | Rose et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,471,953 B1 | 10/2002 | N'Guyen et al. | |
| 6,479,042 B1 | 11/2002 | Nguyen et al. | |
| 6,506,373 B1 | 1/2003 | Dannecker et al. | |
| 6,511,669 B1 | 1/2003 | Garnier et al. | |
| 6,582,477 B1 * | 6/2003 | Plos | 8/405 |
| 6,613,313 B1 | 9/2003 | Kimura | |
| 6,770,271 B1 | 8/2004 | Mondet et al. | |
| 6,824,764 B1 | 11/2004 | Devin-Baudoin et al. | |
| 6,824,765 B1 | 11/2004 | Gawtrey et al. | |
| 6,846,333 B1 * | 1/2005 | Legrand et al. | 8/405 |
| 6,916,467 B1 | 7/2005 | Devin-Baudoin et al. | |
| 2002/0006389 A1 | 1/2002 | Restle et al. | |
| 2002/0187117 A1 | 12/2002 | Devin-Baudoin et al. | |

FOREIGN PATENT DOCUMENTS

| | | |
|---|---|---|
| EP | 0 227 994 | 9/1989 |
| EP | 0 342 834 | 11/1989 |
| EP | 0 486 135 | 5/1992 |
| EP | 0 412 707 | 2/1994 |
| EP | 0 582 152 | 2/1994 |
| EP | 0 646 572 | 4/1995 |
| EP | 0 412 704 | 4/1999 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 9/1977 |
| GB | 1 546 809 | 5/1979 |
| GB | 2 141 454 | 12/1984 |
| GB | 2 165 550 | 4/1986 |
| GB | 2 058 103 | 4/1991 |
| JP | 2001-10935 | 1/2001 |
| WO | WO 93/23446 | 11/1993 |
| WO | WO 94/07844 | 4/1994 |
| WO | WO 94/10131 | 5/1994 |
| WO | WO 94/24097 | 10/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

"Encyclopedia of Chemical Technology", Kirk-Othmer, Third Edition, 1982, vol. 22, pp. 332-433.

"Encyclopedia of Chemical Technology", Kirk-Othmer, Third Edition, 1982, vol. 3, pp. 896-900.

"Industrial Gums—Polysaccharides and their Derivatives", edited by Roy L. Whistler, Second Edition, Academic Press.

"Polymers in Nature", E.A. MacGregor & C.T. Greenwood, John Wiley & Sons, Chapter 6, pp. 240-328, 1980.

"Volatile Silicone Fluids for Cosmetic Formulations", Cosmetics and Toiletries, vol.91, Jan. 1976, pp. 27-32.

Copending Appl. No. 10/290,149, filed Nov. 8, 2002.
Copending Appl. No. 10/290,159, filed Nov. 8, 2002.
Copending Appl. No. 10/290,189, filed Nov. 8, 2002.
Copending Appl. No. 10/290,192, filed Nov. 8, 2002.
Copending Appl. No. 10/290,208, filed Nov. 8, 2002.
Copending Appl. No. 10/290,226, filed Nov. 8, 2002.
Copending Appl. No. 10/290,341, filed Nov. 8, 2002.
Copending Appl. No. 10/290,342, filed Nov. 8, 2002.
Copending Appl. No. 10/290,343, filed Nov. 8, 2002.
Copending Appl. No. 10/290,345, filed Nov. 8, 2002.
Copending Appl. No. 10/290,348, filed Nov. 8, 2002.
Copending Appl. No. 10/290,409, filed Nov. 8, 2002.
Copending Appl. No. 11/158,014, filed Jun. 22, 2005.
English language Derwent Abstract of DE 197 54 053, Jun. 10, 1999.
English language Derwent Abstract of DE 42 29 922, Mar. 10, 1994.
English language Derwent Abstract of DE 44 02 929, Jun. 22, 1995.
English language Derwent Abstract of DE 44 20 736, Aug. 10, 1995.
English language Derwent Abstract of DE 44 24 530, Jan. 18, 1996.
English language Derwent Abstract of DE 44 24 533, Jan. 18, 1996.
English language Derwent Abstract of EP 0 080 976, Jun. 8, 1983.
English language Derwent Abstract of EP 0 122 324, Oct. 24, 1984.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Derwent Abstract of JP 2001-10936, Jan. 16, 2001.
English language Derwent Abstract of JP 2-250814, Oct. 8, 1990.
English language Derwent Abstract of JP 4-154713, May 27, 1992.
English language Derwent Abstract of JP 8-157340, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
French Search Report for FR 0 114 468, dated Aug. 8, 2002.

French Search Report for FR 0 114 469, dated Aug. 22, 2002.
French Search Report for FR 0 114 470, dated Sep. 18, 2002.
French Search Report for FR 0 114 472, dated Aug. 30, 2002.
French Search Report for FR 0 114 473, dated Sep. 16, 2002.
French Search Report for FR 0 114 474, dated Aug. 8. 2002.
French Search Report for FR 0 114 476, dated Sep. 20, 2002.
French Search Report for FR 0 114 477, dated Sep. 20, 2002.
French Search Report for FR 0 114 478, dated Sep. 18, 2002.
French Search Report for FR 0 114 479, dated Sep. 16, 2002.
French Search Report for FR 0 114 480, dated Aug. 9, 2002.
French Search Report for FR 0 114 481, dated Sep. 4, 2002.
French Search Report for FR 0 114 482, dated Aug. 28, 2002.
French Search Report for FR 0 114 484, dated Sep. 4, 2002.
French Search Report for FR 0 114 485, dated Aug. 29, 2002.
French Search Report for FR 0 114 486, dated Sep. 23, 2002.
P.D. Dorgan "Waxes in Cosmetics", Drug and Cosmetic Industry, Dec. 1983, pp. 30-33.
Porter, M.R., Handbook of Surfactants 116-178 (Blackie & Son 1991).
English language Patent Abstract of Japan of JP 2001-10935, Jan. 16, 2001.
Office Action in co-pending Appl. No. 10/290,149, dated Apr. 30, 2004.
Office Action in co-pending Appl. No. 10/290,149, dated Nov. 4, 2004.
Office Action in co-pending Appl. No. 10/290,159, dated Dec. 27, 2004.
Office Action in co-pending Appl. No. 10/290,159, dated May 3, 2004.
Office Action in co-pending Appl. No. 10/290,189, dated Feb. 16, 2006.
Office Action in co-pending Appl. No. 10/290,192, dated Jan. 11, 2006.
Office Action in co-pending Appl. No. 10/290,208, dated Jan. 11, 2006.
Office Action in co-pending Appl. No. 10/290,341, dated Jan. 11, 2006.
Office Action in co-pending Appl. No. 10/290,342, dated Jan. 25, 2006.
Office Action in co-pending Appl. No. 10/290,343, dated Jan. 25, 2006.
Office Action in co-pending Appl. No. 10/290,345, dated Feb. 9, 2006.

* cited by examiner

OXIDIZING COMPOSITION FOR TREATING KERATIN FIBERS, COMPRISING A PARTICULAR AMINOSILICONE

This disclosure relates to an oxidizing composition for treating human keratin fibres, such as hair, comprising at least one aminosilicone, as defined herein. The present disclosure also relates to the composition's uses for dyeing, permanently reshaping, and bleaching the keratin fibres.

It is a well-known practice to bleach keratin fibres, such as human hair, with bleaching compositions comprising at least one oxidizing agent. Conventional oxidizing agents are chosen, for example, from hydrogen peroxide and compounds capable of producing hydrogen peroxide by hydrolysis, such as urea peroxide and persalts, such as perborates, percarbonates and persulphates. Hydrogen peroxide and persulphates, for example, may be used.

Bleaching compositions may be chosen, for example, from compositions in the form of anhydrous products (powders or creams) comprising alkaline compounds (amines and alkaline silicates), and peroxygenated reagents, such as ammonium and alkali metal persulphates, perborates and percarbonates, which may be diluted with aqueous hydrogen peroxide compositions.

A bleaching composition may also result from the contemporaneous mixing of at least one anhydrous peroxygenated reagent powder with at least one aqueous composition comprising at least one alkaline compound and another aqueous composition comprising hydrogen peroxide.

Bleaching compositions may be, for example, in the form of ready-to-use thickened aqueous hydrogen peroxide compositions.

A "ready-to-use composition" means a composition intended for application as it is to a keratin fibre, e.g., it may be stored before use or may result from the contemporaneous mixing of at least two compositions.

It is a well-known practice to dye keratin fibres, such as human hair, with a dye composition comprising at least one oxidation dye precursor, such as an ortho- or para-phenylenediamine, an ortho- or para-aminophenol, or a heterocyclic compound, which may be known as an oxidation base. At least one oxidation dye precursor, such as an oxidation base, may be, for example, a colourless or a weakly coloured compound. The at least one oxidation dye precursor may be combined with at least one oxidizing agent, which may, for example, yield at least one coloured compound and/or at least one colorant by, for example, oxidative condensation. It is also well-known that a shade obtained with at least one of these oxidation bases may be varied, for example, by combining at least one oxidation base with at least one coupler and/or at least one coloration modifier. At least one coloration modifier may be chosen, for example, from aromatic meta-diamines, meta-aminophenols, meta-diphenols and heterocyclic compounds, such as indole compounds.

The at least one oxidizing agent may be chosen, for example, from oxidizing agents conventionally used for oxidation dyeing of keratin fibres, such as hydrogen peroxide and compounds capable of producing hydrogen peroxide by hydrolysis, such as urea peroxide, and persalts such as perborates and persulphates. The at least one oxidizing agent may comprise, for example, hydrogen peroxide.

It is well-known that a technique for obtaining permanent reshaping of the hair comprises, for example, opening the keratin —S—S-disulphide (cystine) bonds, in a first stage, using a composition comprising at least one suitable reducing agent (e.g., the reduction step), rinsing the hair, reconstituting, in a second stage, the disulphide bonds by applying to the hair, which has, for example, been placed under tension beforehand (e.g., using curlers), an oxidizing composition (e.g., the oxidation step or fixing step) so as finally to give to the hair the desired shape. This technique makes possible, for example, to make the hair wavy or to straighten it by removing the hair's curliness. The new shape given to hair by a chemical treatment such as above may be long-lasting. For example, the new shape may withstand the action of washing with water or shampoos. This technique may be contrasted with a simple standard technique for temporary reshaping, such as hair setting.

A reducing composition that may be used for the first step of a permanent-waving operation may comprise, for example, at least one reducing agent chosen, for example, from sulphites, bisulphites, alkylphosphines, and thiols.

An oxidizing composition used to carry out the fixing step may comprise, for example an aqueous hydrogen peroxide solution.

It is well-known, for example, that the oxidizing treatments in the permanent reshaping of the hair, and above all those involved in dyeing and bleaching, may be aggressive and may lead to poor cosmetic properties of the hair, such as difficulty in disentangling, an unpleasant feel, or coarse, dull hair, or hair charged with static electricity, and to degradation of the fibres.

After considerable research, the inventors have discovered, surprisingly and unexpectedly, that by using at least one aminosilicone chosen from formula (I) and formula (II), defined below, at least one of these drawbacks may be overcome, with conditioning and remanent effects that can be superior to those of the systems previously used, without, however, impairing the intensity and homogeneity of permanent-reshaping, dyeing and bleaching results.

The condition of a keratin fibre, such as human hair, may thus be improved.

The phrase "improvement in the condition of the fibre" may mean, for example, at least one of the following: a reduction in the porosity or the alkaline solubility of the fibre or an improvement in the cosmetic properties, such as smoothness, softness and ease of disentangling and of styling.

This effect may be, for example, remnant, i.e. long-lasting.

The porosity is measured by fixing at 37° C. and at pH 10, for 2 minutes, 2-nitro-para-phenylenediamine at 0.25% in an ethanol/pH 10 buffer mixture (10/90 volume ratio).

The alkaline solubility corresponds, for example, to the loss of mass of a sample of 100 mg of keratin fibres under the action of decinormal sodium hydroxide for 30 minutes at 65° C.

Another new embodiment is a cosmetic composition for treating keratin fibres, such as human hair, comprising, in a cosmetically acceptable medium:

(i) at least one oxidizing agent, and (ii) at least one aminosilicone chosen from formula (I) and (II).

At least one other characteristic, aspect, subject and advantage of the embodiments disclosed herein will become apparent to one having ordinary skill in the art upon reading the description and the examples that follow without, however, exhibiting a limiting character.

Aminosilicone(s)

The at least one aminosilicone is chosen from formulae (I) and (II):

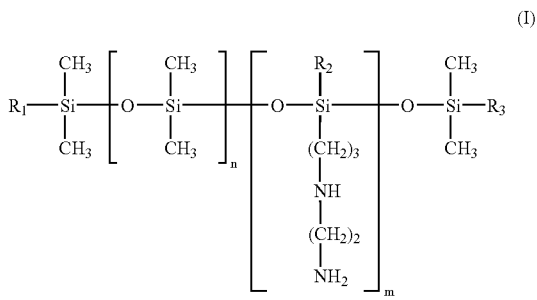

(I)

wherein:
- m and n are numbers with a sum (n+m) ranging from 1 to 1000, for example from 50 to 250, and further, for example, from 100 to 200;
- n ranges from 0 to 999 and, for example from 49 to 249, and further, for example, from 125 to 175, and m ranges from 1 to 1000, for example from 1 to 10, and further, for example, from 1 to 5;
- $R_1$, $R_2$ and $R_3$, which may be identical or different, are chosen from hydroxyl and $C_1$–$C_4$ alkoxy radicals, wherein at least one of the radicals $R_1$ to $R_3$ are chosen from alkoxy radicals.

The alkoxy radical may be, for example, a methoxy radical.

The hydroxyl/alkoxy molar ratio may range from 0.2:1 to 0.4:1, and further, for example, from 0.25:1 to 0.35:1, and still further, may be equal to 0.3.

The at least one aminosilicone of formula (I) may have, for example, a weight-average molecular mass ranging from 2000 to 1 000 000, such as from 3500 to 200 000.

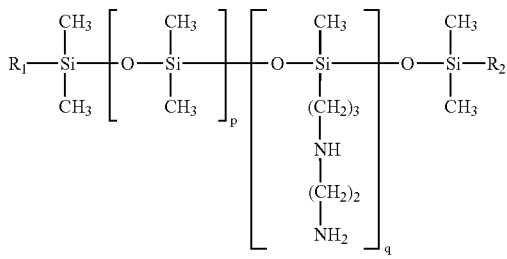

(II)

wherein:
- p and q are numbers with a sum (p+q) ranging from 1 to 1000, for example, from 50 to 350, such as from 150 to 250
- p is a number ranging from 0 to 999, for example from 49 to 349, and further, for example, from 159 to 239, and q is a number ranging from 1 to 1000, for example from 1 to 10, and further, for example, from 1 to 5;
- $R_1$ and $R_2$, which are different, are chosen from hydroxyl radicals and $C_1$–$C_4$ alkoxy radicals, at least one of the radicals $R_1$ and $R_2$ denoting an alkoxy radical.

The alkoxy radical may be, for example, a methoxy radical.

The hydroxyl/alkoxy molar ratio may range, for example, from 1:0.8 to 1:1.1, and further, for example, from 1:0.9 to 1:1, and still further, for example, may be equal to 1:0.95.

The aminosilicone of formula (II) may have a weight-average molecular mass, for example, ranging from 2000 to 200 000, and further, for example, from 5000 to 100 000, and still further from 10 000 to 50 000.

The weight-average molecular masses of these aminosilicones are measured by Gel Permeation Chromatography (GPC) at room temperature, as polystyrene equivalents. The columns used are styragel μ columns. The eluent is THF and the flow rate is 1 ml/minute. 200 μl of a solution at 0.5% by weight of silicone in THF are injected. The detection is performed by refractometry and UV-metry.

A commercial product comprising at least one aminosilicone chosen from formula (I) and (II) may comprise at least one additional aminosilicone whose structure is different from those of formula (I) and (II).

At least one aminosilicone of formula (I) is sold, for example, by the company Wacker under the name Belsil ADM 652®.

At least one aminosilicone of formula (II) may be chosen, for example, from products sold by the company Wacker under the names Fluid WR 1300® and Belsil ADM 6057®.

In another new embodiment, at least one aminosilicone of formula (I) or (II) is present in the form of an oil-in-water emulsion. The oil-in-water emulsion may further comprise, for example, at least one surfactant. The at least one surfactant may be chosen, for example, from cationic surfactants and non-ionic surfactants.

The aminosilicone particles in the emulsion may have, for example, a mean particle size ranging from 3 to 500 nanometres. Such particle sizes are measured with a laser granulometer.

A micro emulsion comprising, for example, at least one aminosilicone of formula (II) may have particle sizes ranging from 5 to 60 nanometres, such as from 10 to 50 nanometres.

The micro emulsion comprising at least one aminosilicone of formula (II) may be chosen, for example, from products sold under the name Finish CT 96 E® or SLM 28020® by the company Wacker.

At least one aminosilicone of formula (I) and (II) may be chosen, for example, such that the contact angle with water of a hair treated with a composition comprising 2% AM (active materials) of the at least one aminosilicone ranges from 90 to 180°, such as from 90 to 130°.

A composition comprising at least one aminosilicone of formula (I) or (II) may be chosen, for example, such that the contact angle of a hair treated with the composition ranges from 90 to 180°, such as from 90 to 130°.

The contact angle measurement may be based, for example, on immersing a hair in distilled water. The method of measurement comprises evaluating the force exerted by the water on the hair during its immersion in distilled water and during its removal. The forces thus measured may be linked to the contact angle θ between the water and the surface of the hair. The hair is hydrophilic when the angle θ ranges from 0 to less than 90°, and hydrophobic when this angle ranges from 90° to 180°.

The test is carried out with locks of natural hair that have been bleached under the same conditions and then washed.

Each 1 g lock is placed in a crystallizing dish 75 mm in diameter and then covered uniformly with 5 ml of the test formulation. The lock is thus left for 15 minutes at room temperature and then rinsed for 30 seconds. The drained lock is left in the open air until it is completely dry.

For each evaluation, 10 hairs that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of the hair is measured by means of observation by microscope.

The mean wet ability force on 10 hairs and the cross section of the analysed hairs make it possible to obtain the contact angle of the hair on the water, according to the formula:

$$F = P * \lceil lv * \cos\theta$$

where F is the wet ability force expressed in newtons, P is the perimeter of the hair in metres, $\lceil lv$ is the liquid/water vapour interface tension in $J/m^2$ and $\theta$ is the contact angle.

The product SLM 28020® from Wacker at 12% in water (i.e. 2% aminosilicone) gives a contact angle of 93° according to the test indicated above.

In another embodiment, the oxidizing composition may comprise, for example, at least one aminosilicone chosen from formula (I) and (II) in an amount ranging from 0.01% to 20% by weight, relative to the total weight of the composition. The composition may comprise, for example, the at least one aminosilicone chosen from formula (I) and (II) in an amount ranging from 0.1% to 15% by weight, such as from 0.5% to 10% by weight.

Oxidizing Agent(s)

At least one oxidizing agent may be chosen, for example, from hydrogen peroxide and compounds capable of producing hydrogen peroxide by hydrolysis, and mixtures thereof.

The at least one oxidizing agent may be chosen, for example, from aqueous hydrogen peroxide solutions, urea peroxide, and persalts such as perborates and persulphates, and mixtures thereof.

The at least one oxidizing agent may comprise hydrogen peroxide, and for example, the at least one oxidizing agent may also comprise an aqueous hydrogen peroxide solution.

The hydrogen peroxide concentration may range, for example, from 0.5 to 40 volumes, such as from 2 to 30 volumes. The concentration of at least one compound capable of forming hydrogen peroxide by hydrolysis may range, for example, from 0.1% to 25% by weight, relative to the total weight of the oxidizing composition.

The at least one oxidizing composition may be, for example, an anhydrous composition or an aqueous composition.

The at least one oxidizing agent may comprise, for example, an aqueous composition, and the pH of the aqueous composition may range, for example, from 1 to 13, such as from 2 to 12.

An oxidizing composition comprising at least one oxidizing agent may also be in two parts to be mixed together contemporaneously at the time of use, one of these two parts comprising at least one alkaline agent chosen from agents in solid and liquid forms. For hydrogen peroxide, the pH may be, for example, below 7 before mixing.

The pH of an aqueous oxidizing composition comprising at least one oxidizing agent may be obtained and/or adjusted by adding at least one basifying agent chosen, for example, from aqueous ammonia, monoethanolamine, diethanolamine, triethanolamine, isopropanolamine, 1,3-propanediamine, alkali metals and ammonium carbonate and bicarbonate, organic carbonates, such as guanidine carbonate, and alkali metal hydroxides, and mixtures thereof, and/or by adding at least one acidifying agent chosen, for example, from hydrochloric acid, acetic acid, lactic acid and boric acid.

An oxidizing composition may comprise, for example, at least one additive chosen from additives well-known for their use in oxidizing compositions for dyeing the hair by oxidation, for permanently reshaping or bleaching the hair, such as acidifying and basifying agents, preserving agents and sequestering agents.

If the at least one oxidizing agent comprises an aqueous hydrogen peroxide solution, the oxidizing composition may comprise, for example, at least one stabilizer for aqueous hydrogen peroxide solution. A composition comprising an aqueous hydrogen peroxide solution and at least one amphiphilic polymer may further comprise at least one stabilizer chosen, for example, from alkali metal and alkaline-earth metal pyrophosphates, alkali metal and alkaline-earth metal stannates, phenacetin and acid salts of oxyquinoline, such as oxyquinoline sulphate. The composition may comprise, for example, at least one stannate optionally combined with at least one pyrophosphate.

In an oxidizing composition, the concentration of the at least one stabilizer for the aqueous hydrogen peroxide solution may range, for example, from 0.0001% to 5% by weight, such as from 0.01% to 2% by weight relative to the total weight of the oxidizing compositions.

In an oxidizing composition comprising an aqueous hydrogen peroxide solution, the concentration ratio of hydrogen peroxide to the at least one stabilizer may range, for example, from 0.05:1 to 1000:1, and further, for example from 0.1:1 to 500:1, and still further, for example, from 1:1 to 200:1. A concentration ratio of the at least one aminosilicone to the at least one oxidizing agent may range, for example, from 0.001:1 to 10:1, the amount of the at least one aminosilicone and the at least one oxidizing agent being expressed as active materials (e.g., hydrogen peroxide for the aqueous hydrogen peroxide solution). This ratio may range, for example, from 0.01 to 5, such as from 0.02 to 1:1.

Cosmetically Acceptable Medium

The medium for the cosmetically acceptable composition may comprise at least one medium chosen, for example, from aqueous media comprising water and cosmetically acceptable organic solvents, for example alcohols, such as ethanol, isopropyl alcohol, benzyl alcohol and phenyl ethyl alcohol, and glycols and glycol ethers, such as ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether. At least one solvent may, for example, be present in an amount ranging from 0.5% to 20%, such as from 2% to 10% by weight, relative to the total weight of the composition.

Ingredient(s)

The composition may also comprise at least one agent for adjusting the rheology. The at least one agent may be chosen, for example, from cellulosic thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), and synthetic thickeners, such as cross linked homopolymers of acrylic acid and cross-linked homopolymers of acrylamidopropanesulphonic acid.

In another embodiment, the composition may comprise, for example, at least one ionic associative polymer and/or at least one nonionic associative polymer chosen, for example, from the polymers sold under the names Pemulen® TR1 or TR2 by the company Goodrich, Salcare SC 90® by the company Allied Colloids, Aculyn® 22, 28, 33, 44 or 46 by the company Rohm & Haas, and Elfacos® T210 and T212 by the company Akzo. The at least one ionic associative polymer and/or at least one nonionic associative polymer may be present in an amount ranging, for example, from 0.01% to 10% by weight, relative to the total weight of the composition.

In another new embodiment, the composition may comprise, for example, at least one cationic or amphoteric polymer in an amount ranging, for example, from 0.01% to 10% by weight, and further, for example, from 0.05% to 5%, and still further, for example, from 0.1% to 3%, relative to the total weight of the composition.

Cationic Polymer(s)

The phrase "cationic polymer" means, for example, any polymer comprising at least one cationic monomeric unit and/or at least one monomeric unit that may be ionized into at least one cationic group.

At least one cationic polymer may be chosen, for example, from polymers described in Patent Application No. EP-A-337 354 and in French Patent Nos. FR-2 270 846, 2 383 660, 2 598 611, 2 470 596 and 2 519 863.

At least one cationic polymer may be chosen, for example, from polymers comprising monomeric units comprising primary, secondary, tertiary and quaternary amine groups, which may form part of the main polymer chain and may be attached to a side substituent attached to the main polymer chain.

The at least one cationic polymer may, for example, have a number-average molecular mass ranging from 500 to $5 \times 10^6$, such as from $10^3$ to $3 \times 10^6$.

The at least one cationic polymer may be chosen, for example, from polymers of the polyamine, polyamino amide, and polyquaternary ammonium types.

The at least one cationic polymer may be chosen, for example, from polymers described in French Patent Nos. 2 505 348 and 2 542 997. The at least one cationic polymer may be chosen, for example, from:

(1) homopolymers or copolymers derived from acrylic or methacrylic esters and amides and comprising at least one of the units of formula (I), (II), (III) or (IV) below:

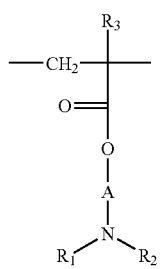
(I)

-continued

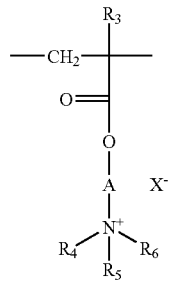
(II)

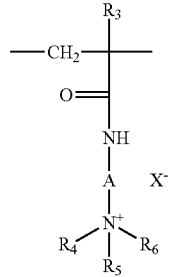
(III)

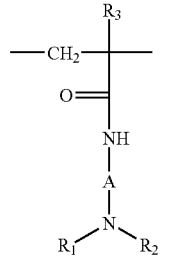
(IV)

wherein:

$R_3$, which may be identified or different, is chosen from a hydrogen atom and $CH_3$ radical;

A, which may be identical or different, is chosen from linear and branched alkyl groups comprising from 1 to 6 carbon atoms, such as 2 or 3 carbon atoms, and hydroxyalkyl groups comprising from 1 to 4 carbon atoms;

$R_4$, $R_5$ and $R_6$, which may be identical or different, are chosen from alkyl groups comprising from 1 to 18 carbon atoms and a benzyl radical and, for example, alkyl groups comprising from 1 to 6 carbon atoms;

$R_1$ and $R_2$, which may be identical or different, are chosen from hydrogen and alkyl groups comprising from 1 to 6 carbon atoms, such as methyl and ethyl groups;

$X^-$ is chosen from anions derived from inorganic and organic acids, such as a methosulphate anion and halides, such as chloride and bromide.

At least one polymer of family (1) may also comprise at least one monomeric unit derived from comonomers which may be chosen, for example, from acrylamides, methacrylamides, diacetoneacrylamides, acrylamides and methacrylamides substituted on the nitrogen with lower ($C_1$–$C_4$) alkyls, acrylic and methacrylic acids and esters thereof, vinyllactams such as vinylpyrrolidone and vinylcaprolactam, and vinyl esters.

At least one polymer of family (1) may be chosen, for example, from:
copolymers of acrylamide and of dimethylaminoethyl methacrylate quaternized with dimethyl sulphate and with dimethyl halides, such as the product sold under the name Hercofloc by the company Hercules, copolymers of acryl amide and of methacryloyloxyethyltrimethylammonium chloride described, for example, in Patent Application No. EP-A-080 976 and sold, for example, under the name Bina Quat P 100 by the company Ciba Geigy, the copolymer of acrylamide and of methacryloyloxyethyltrimethylammonium methosulphate sold, for example, under the name Reten by the company Hercules, quaternized and non-quaternized vinylpyrrolidone/dialkylaminoalkyl acrylates and methacrylate copolymers, such as the products sold under the name "Gafquat" by the company ISP, such as "Gafquat 734" and "Gafquat 755", and products known as "Copolymer 845, 958 and 937". These polymers are described in detail in French Patent Nos. 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold, for example, under the name Styleze CC 10 by ISP, and quaternized vinylpyrrolidone/dimethylaminopropylmethacrylamide copolymers, such as the product sold under the name "Gafquat HS 100" by the company ISP.

(2) Cellulose ether derivatives comprising quaternary ammonium groups, described in French Patent No. 1 492 597 and, for example, the polymers sold under the names "JR" (JR 400, JR 125 and JR 30M) or "LR" (LR 400, or LR 30M) by the company Union Carbide Corporation. These polymers may also be defined in the CTFA dictionary as quaternary ammoniums of hydroxyethylcellulose reacted with epoxides substituted with a trimethylammonium group.

(3) Cationic cellulose derivatives, such as cellulose copolymers and cellulose derivatives grafted with a water-soluble monomer of quaternary ammonium, and described, for example, in U.S. Pat. No. 4,131,576, such as hydroxyalkylcelluloses, for example hydroxymethyl-, hydroxyethyl- and hydroxypropylcelluloses grafted, for example, with a methacryloyloxyethyltrimethylammonium, methacrylamidopropyltrimethyl ammonium or dimethyldiallylammonium salt.

At least one commercial product of this definition may be chosen, for example, from the products sold under the names "Celquat L 200" and "Celquat H 100" by the company National Starch.

(4) Cationic polysaccharides described, for example, in U.S. Pat. Nos. 3,589,578 and 4,031,307, such as guar gums comprising cationic trialkylammonium groups. Guar gums modified with salts (e.g., chloride) of 2,3-epoxypropyltrimethyl ammonium may be used, for example.

At least one cationic polysaccharide may be chosen, for example, from products sold under the trade names Jaguar C13 S, Jaguar C 15, Jaguar C 17 or Jaguar C162 by the company Meyhall.

(5) Polymers comprising piperazinyl units and of divalent alkylene or hydroxyalkylene radicals comprising straight and branched chains, optionally interrupted by at least one atom chosen from oxygen, sulphur and nitrogen atoms, and by aromatic and heterocyclic rings, and also the oxidation and quaternization products of these polymers. Such polymers are described, for example, in French Patent Nos. 2 162 025 and 2 280 361.

(6) Water-soluble polyamino amides prepared, for example, by polycondensation of acidic compounds with polyamines. At least one of these polyamino amides may be cross linked, for example, with at least one cross linking agent chosen, for example, from epihalohydrins, diepoxides, dianhydrides, unsaturated dianhydrides, bis-unsaturated derivatives, bis-halohydrins, bis-azetidiniums, bis-haloacyldiamines, bis-alkyl halides, and oligomers resulting from the reaction of difunctional compounds reactive with bis-halohydrins, bis-azetidiniums, bis-haloacyldiamines, bis-alkyl halides, epihalohydrins, diepoxides and bis-unsaturated derivatives. The at least one cross linking agent may be present in an amount ranging, for example, from 0.025 to 0.35 mol per amine group of the polyamino amide. At least one polyamino amide may be alkylated. If at least one polyamino amide comprises at least one tertiary amine function, the at least one polyamino amide may be quaternized. Such polymers are described, for example, in French Patent Nos. 2 252 840 and 2 368 508.

(7) Polyamino amide derivatives resulting from the condensation of polyalkylene polyamines with polycarboxylic acids followed by alkylation with difunctional agents. At least one polyamino amide derivative may be chosen, for example, from adipic acid/dialkylaminohydroxyalkyl-dialkylenetriamine polymers wherein the alkyl radicals comprise from 1 to 4 carbon atoms, such as methyl, ethyl and propyl radicals. Such polymers are described, for example, in French Patent No. 1 583 363.

At least one polyamino amide derivative may be chosen, for example, from adipic acid/dimethylaminohydroxypropyl/diethylenetriamine polymers sold under the name "Cartaretine F, F4 or F8" by the company Sandoz.

(8) Polymers obtained by reaction of polyalkylene polyamines comprising two primary amine groups and at least one secondary amine group with dicarboxylic acids chosen, for example, from diglycolic acid and saturated aliphatic dicarboxylic acids comprising from 3 to 8 carbon atoms. The molar ratio of at least one polyalkylene polyamine to at least one dicarboxylic acid may range, for example, from 0.8:1 to 1.4:1; a polyamino amide resulting therefrom may be reacted with epichlorohydrin in a molar ratio of epichlorohydrin relative to the secondary amine group of the polyamino amide ranging, for example, from 0.5:1 to 1.8:1. Such polymers are described, for example, in U.S. Pat. Nos. 3,227,615 and 2,961,347.

At least one polymer of this type may be chosen, for example, from products sold under the name "Hercosett 57" by the company Hercules Inc. and under the name "PD 170" or "Delsette 101" by the company Hercules in the case of the adipic acid/epoxypropyl/diethylenetriamine copolymer.

(9) Cyclopolymers of alkyldiallylamine and of dialkyldiallyl ammonium, such as homopolymers and copolymers comprising, as main constituents of the chain, monomeric units of formula (V) or (VI):

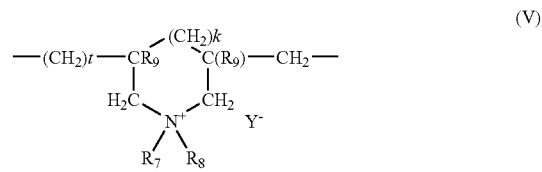

-continued

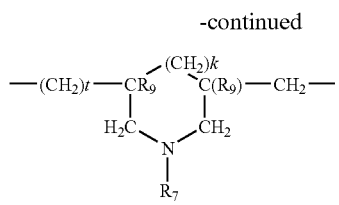
(VI)

wherein k and t are chosen from 0 and 1, the sum k+t being equal to 1; $R_9$ is chosen from a hydrogen atom and a methyl radical; $R_7$ and $R_8$, which may be identical or different, may be chosen, for example, from alkyl groups comprising from 1 to 8 carbon atoms, hydroxyalkyl groups wherein the alkyl groups comprise, for example, from 1 to 5 carbon atoms, lower $C_1$–$C_4$ amidoalkyl groups; $R_7$ and $R_8$, which may be identical or different, may comprise, together with the nitrogen atom to which they are attached, at least one heterocyclic group such as a piperidyl or morpholinyl; $R_7$ and $R_8$, which may be identical or different, may be chosen, for example, from alkyl groups comprising from 1 to 4 carbon atoms; $Y^-$ is chosen from anions, such as bromide, chloride, acetate, borate, citrate, tartrate, bisulphate, bisulphite, sulphate and phosphate. These polymers are described, for example, in French Patent No. 2 080 759 and in its Certificate of Addition 2 190 406.

At least one of the polymers defined above may be chosen, for example, from the dimethyldiallylammonium chloride homopolymers sold under the name "Merquat 100" by the company Calgon (and its homologues of low weight-average molecular mass) and copolymers of diallyidimethyl ammonium chloride and of acryl amide, sold under the name "Merquat 550".

(10) Quaternary diammonium polymers comprising repeating units of the formula:

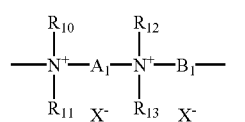
(VII)

wherein:

$R_{10}$, $R_{11}$, $R_{12}$ and $R_{13}$, which may be identical or different, may be chosen, for example, from aliphatic, alicyclic and arylaliphatic radicals comprising from 1 to 20 carbon atoms and lower hydroxyalkylaliphatic radicals; $R_{10}$, $R_{11}$, $R_{12}$ and $R_{13}$, together or separately, constitute, with the nitrogen atoms to which they are attached, a heterocycle optionally comprising at least one additional heteroatom other than nitrogen; $R_{10}$, $R_{11}$, $R_{12}$ and $R_{13}$, which may be identical or different, may be chosen, for example, from linear and branched $C_1$–$C_6$ alkyl radicals substituted with at least one group chosen from nitrile, ester, acryl and amide groups, and groups of the following formulae: —CO—O—$R_{14}$-D and —CO—NH—$R_{14}$—D wherein $R_{14}$ is chosen from alkylenes and D is chosen from quaternary ammonium groups;

$A_1$ and $B_1$ are chosen from polymethylene groups comprising from 2 to 20 carbon atoms, which may be linear and branched, saturated and unsaturated, and which may comprise, linked to and intercalated in the main chain, at least one aromatic ring and at least one atom chosen from oxygen and sulphur atoms, and at least one group chosen from sulphoxide, sulphone, disulphide, amino, alkylamino, hydroxyl, quaternary ammonium, ureido, amide and ester groups, and $X^-$ is chosen from anions derived from mineral and organic acids;

$A_1$, $R_{10}$ and $R_{12}$ may also comprise, with the two nitrogen atoms to which they are attached, at least one piperazine ring; if $A_1$ is chosen from linear and branched, saturated and unsaturated alkylenes and hydroxyalkylene radicals, $B_1$ may be chosen from groups of the following formula —$(CH_2)_n$—CO-D-OC—$(CH_2)_n$—wherein n ranges from 1 to 100such as from 1 to 50, and D is chosen from:

a) glycol residues of formula: —O-Z-O—, wherein Z is chosen from linear and branched hydrocarbon-based radicals and groups of the following formulae:

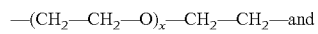

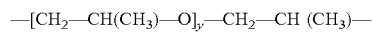

wherein x and y, which may be identical or different, are integers ranging from 1 to 4, representing a defined and unique degree of polymerisation or any number ranging from 1 to 4 representing an average degree of polymerisation;

b) a bis-secondary diamine residue such as a piperazine derivative;

c) a bis-primary diamine residue of formula: —NH—Y—NH—, wherein Y is chosen from linear and branched hydrocarbon-based radicals, and the divalent radical

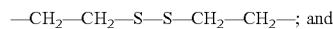

d) a ureylene group of formula: —NH—CO—NH—.

$X^{31}$ may be chosen, for example, from anions, such as chloride or bromide.

These polymers may have, for example, a number-average molecular mass ranging from 1000 to 100 000.

These polymers are described, for example, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Polymers that are comprised of repeating units of formula (VIII) below can be used:

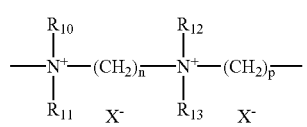
(VIII)

wherein $R_{10}$, $R_{11}$, $R_{12}$ and $R_{13}$, which may be identical or different, are chosen from alkyl and hydroxyalkyl radicals comprising from 1 to 4 carbon atoms, n and p, which may be identical or different, are integers ranging from 2 to 20, and $X^-$ is chosen from anions derived from mineral and organic acids. For example, where $R_{10}$, $R_{11}$, $R_{12}$ and $R_{13}$ are each a methyl radical, n=3, p=6, and X=Cl, this is known as hexadimethine chloride, according to the INCI (CFTA) nomenclature.

(11) Polyquaternary ammonium polymers comprising repeating units of formula (IX):

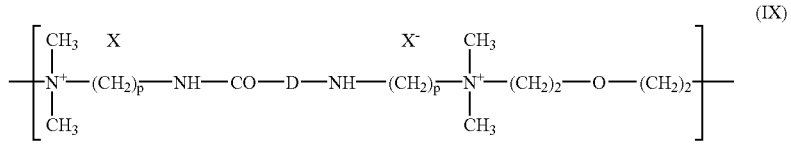

wherein p is an integer ranging from 1 to 6, D may be nothing or may be chosen from a group —(CH$_2$)$_r$—CO— wherein r may be a number equal to 4 or 7, and X$^-$ comprises an anion.

Such polymers may be prepared, for example, according to the processes described in U.S. Pat. Nos. 4,157,388, 4,702,906 and 4,719,282. They are also described, for example, in European Patent Application No. EP-A-1 22 324.

Among these polymers, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as the products sold, for example, under the names Luviquat FC 905, FC 550 and FC 370 by the company BASF.

(13) Polyamines, such as Polyquart H sold by Henkel, for example those sold under the reference name "Polyethylene glycol (15) tallow polyamine" in the CTFA dictionary.

(14) Cross linked methacryloyloxy(C$_1$–C$_4$)alkyltri (C$_1$–C$_4$)alkylammonium salt polymers such as the polymers obtained by homopolymerization of dimethylaminoethyl methacrylate quaternized with methyl chloride, or by copolymerisation of acryl amide with dimethylaminoethyl methacrylate quaternized with methyl chloride, the homo- or copolymerisation being followed by cross linking with a compound comprising olefinic unsaturation, such as methylenebisacrylamide. A cross linked acrylamide/methacryloyloxyethyltrimethylammonium chloride copolymer (20/80 by weight) in the form of a dispersion comprising 50% by weight of the copolymer in mineral oil, for example, can be used. This dispersion is sold, for example, under the name "Salcare® SC 92" by the company Allied Colloids. A cross linked methacryloyloxyethyltrimethyl ammonium chloride homopolymers comprising 50% by weight of the homopolymer in mineral oil or in a liquid ester can also be used. These dispersions are sold under the names "Salcare® SC 95" and "Salcare® SC 96" by the company Allied Colloids.

The at least one cationic polymer may be chosen, for example, from polyalkyleneimines, such as polyethyleneimines, polymers comprising vinylpyridine and vinylpyridinium units, condensates of polyamines and of epichlorohydrin, quaternary polyureylenes and chitin derivatives.

The at least one cationic polymer may be chosen, for example, from the polymers of families (1), (9), (10), (11) and (14), such as the polymers comprising monomeric units of formulae (W) and (U):

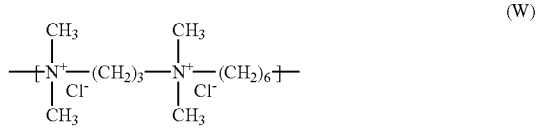

and, for example, those polymers comprising monomeric units of formula (W), whose weight-average molar mass, determined by gel permeation chromatography, may range, for example, from 9500 to 9900;

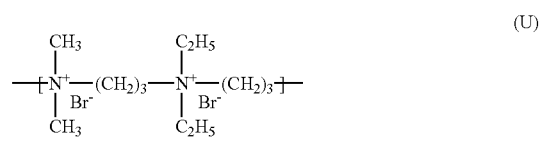

and, for example, those polymers comprising monomeric units of formula (U), whose weight-average molar mass, determined by gel permeation chromatography, may be, for example, 1200.

The concentration of the at least one cationic polymer may range from 0.01% to 10% by weight relative to the total weight of the composition, for example from 0.05% to 5%, and further, for example, from 0.1% to 3%.

Amphoteric Polymer(s)

The at least one amphoteric polymer may be chosen, for example, from polymers comprising units K and M randomly distributed in the polymer chain, wherein K comprises a unit derived from a monomer comprising at least one basic nitrogen atom, and M comprises a unit derived from an acidic monomer comprising at least one carboxylic or sulphonic group, or K and M may be chosen from groups derived from zwitterionic carboxybetaine and sulphobetaine monomers.

K and M may also be chosen from cationic polymer chains comprising at least one group chosen from primary, secondary, tertiary and quaternary amine groups, wherein at least one of the amine groups bears at least one group chosen from carboxylic and sulphonic groups linked via a hydrocarbon-based radical, or K and M can form part of a chain of a polymer comprising an α,β-dicarboxylic ethylene unit wherein one of the carboxylic groups has been made to react with a polyamine comprising at least one amine chosen from primary and secondary amine groups.

The amphoteric polymers of the above definition may be chosen, for example, from the following polymers:

(1) polymers resulting from the copolymerisation of at least one monomer derived from a vinyl compound bearing a carboxylic group, such as acrylic acid, methacrylic acid, maleic acid, α-chloroacrylic acid, and at least one basic monomer derived from a substituted vinyl compound comprising at least one basic atom, such as dialkylaminoalkyl methacrylate and acrylate, dialkylaminoalkylmethacrylamide and -acrylamide. Such compounds are described, for example, in U.S. Pat. No. 3,836,537.

Mention may also be made, for example, of the sodium acrylate/acrylamidopropyltrimethyl ammonium chloride copolymer sold under the name Polyquart KE 3033 by the company Henkel.

At least one vinyl compound may also comprise a dialkyldiallyl ammonium salt, such as dimethyldiallylammonium chloride. The copolymers of acrylic acid and of the latter monomer are sold, for example, under the names Merquat 280, Merquat 295 and Merquat Plus 3330 by the company Calgon.

(2) polymers comprising units derived from:

a) at least one monomer chosen from acrylamides and methacrylamides substituted on the nitrogen with an alkyl radical, b) at least one acidic comonomer comprising at least one reactive carboxylic group, and c) at least one basic comonomer such as esters comprising substituents chosen from primary, secondary, tertiary and quaternary amine substituents of acrylic and methacrylic acids and the products of quaternization of dimethylaminoethyl methacrylate with dimethyl and diethyl sulphates.

At least one N-substituted acryl amide or at least one methacrylamide may be chosen, for example, from groups wherein the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

At least one acidic comonomer may be chosen, for example, from acrylic acid, methacrylic acid, crotonic acid, itaconic acid, maleic acid and fumaric acid and alkyl monoesters, comprising 1 to 4 carbon atoms, of maleic and fumaric acids and anhydrides.

At least one basic comonomer may be chosen, for example, from amino ethyl, butylaminoethyl, N,N'-dimethylaminoethyl and N-tert-butylaminoethyl methacrylates.

At least one copolymer whose CTFA (4th edition, 1991) name is octylacrylamide/acrylates/butylaminoethyl methacrylate copolymer, such as the products sold under the name Amphomer or Lovocryl 47 by the company National Starch, may be used.

(3) cross linked and alkylated polyamino amides partially or totally derived from polyamino amides of formula:

$$\text{—[CO—R}_{19}\text{-CO—Z]—} \qquad (X)$$

wherein $R_{19}$ is chosen from divalent radicals derived from saturated dicarboxylic acids, a mono- or dicarboxylic aliphatic acids comprising at least one ethylenic double bond, esters of lower alkanols, comprising 1 to 6 carbon atoms, of these acids and radicals derived from the addition of any one of the acids to bis(primary) and bis(secondary) amines, and Z may be chosen from bis(primary), mono- and bis(secondary) polyalkylene-polyamine radicals and may be chosen, for example, from:

a) in proportions ranging from 60 to 100 mol %, the radicals

(XI)

wherein x=2 and p=2 or 3, or x=3 and p=2 these radicals being derived from diethylenetriamine, from triethylenetetraamine and from dipropylenetriamine;

b) in proportions ranging from 0 to 40 mol %, the radicals (XI) wherein x=2 and p=1 and which are derived from ethylenediamine, and the radicals derived from piperazine:

c) in proportions ranging from 0 to 20 mol %, the —NH—$(CH_2)_6$—NH— radicals derived from hexamethylenediamine, these polyamino amines being cross linked by addition of difunctional cross linking agents chosen from epihalohydrins, diepoxides, dianhydrides and bis-unsaturated derivatives, using from 0.025 to 0.35 mol of cross linking agent per amine group of the polyamino amide and alkylated by the action of acrylic acid, chloroacetic acid and alkane sultones, and salts thereof.

At least one saturated carboxylic acid may be chosen, for example, from acids comprising 6 to 10 carbon atoms, such as adipic acid, 2,2,4-trimethyladipic acid and 2,4,4-trimethyladipic acid, terephthalic acid, and acids comprising an ethylenic double bond such as, for example, acrylic acid, methacrylic acid and itaconic acid.

At least one alkane sultone used in the alkylation may be chosen, for example, from propane sultone and butane sultone, wherein at least one salt of the alkylating agents may be chosen, for example, from sodium and potassium salts.

(4) polymers comprising zwitterionic units of formula:

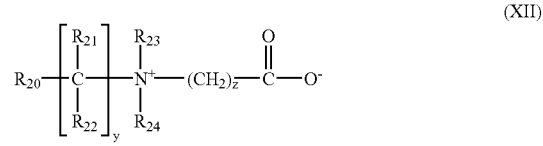

(XII)

wherein $R_{20}$ is chosen, for example, from polymerizable unsaturated groups, such as an acrylate, methacrylate, acryl amide or methacrylamide groups, y and z, which may be identical or different, are chosen from integers from 1 to 3, $R_{21}$ and $R_{22}$ are chosen from a hydrogen atom, methyl, ethyl and propyl radicals, $R_{23}$ and $R_{24}$ are chosen from a hydrogen atom and alkyl radicals, such that the sum of the carbon atoms in $R_{23}$ and $R_{24}$ does not exceed 10.

The polymers comprising such monomeric units may also comprise at least one monomeric unit chosen from monomers derived from non-zwitterionic monomers, such as dimethyl and diethylaminoethyl acrylate and methacrylate and alkyl acrylates and methacrylates, acrylamides and methacrylamides and vinyl acetate.

Mention may be made, for example, of the copolymer of butyl methacrylate/dimethylcarboxymethylammonioethylmethacrylate, such as the product sold under the name Diaformer Z301 by the company Sandoz.

(5) polymers derived from chitosan comprising monomer units of formulae (XIII), (XIV) and (XV):

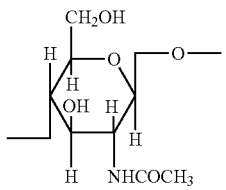
(XIII)

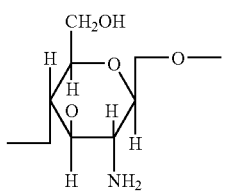
(XIV)

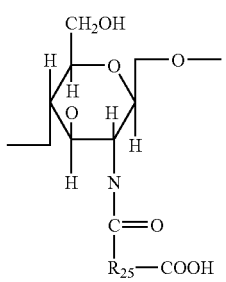
(XV)

the unit (XIII) being present in an amount ranging from 0 to 30%, the unit (XIV) being present in an amount ranging from 5% to 50%, and the unit (XV) being present in an amount ranging from 30% to 90%, wherein, $R_{25}$, in the unit (XV), is chosen from radicals of formula:

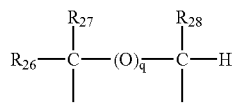

wherein q is 0 or 1;

if q=0, $R_{26}$, $R_{27}$ and $R_{28}$, which may be identical or different, each are chosen from a hydrogen atom, methyl, hydroxyl, acetoxy and amino residues, monoalkylamine residues and dialkylamine residues which are optionally interrupted by at least one nitrogen atom and optionally substituted with at least one group chosen from amine, hydroxyl, carboxyl, alkylthio and sulphonic groups, alkylthio residues wherein at least one alkyl group bears an amino residue, and at least one of the radicals $R_{26}$, $R_{27}$ and $R_{28}$ being a hydrogen atom;

or, if q=1, $R_{26}$, $R_{27}$ and $R_{28}$ each are chosen from a hydrogen atom, and the acid and base salts formed by these compounds.

(6) polymers derived from the N-carboxyalkylation of chitosan, such as N-carboxymethylchitosan and N-carboxybutylchitosan sold, for example, under the name "Evalsan" by the company Jan Dekker.

(7) polymers of formula (XI) described, for example, in French Patent No. 1 400 366:

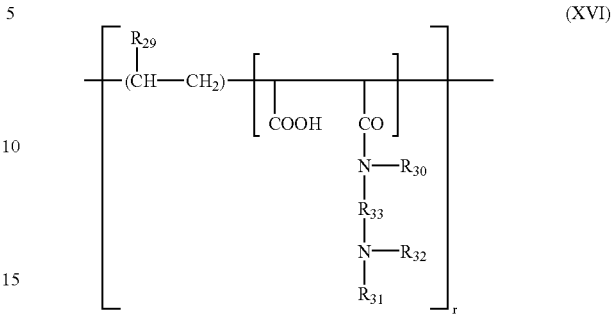
(XVI)

wherein $R_{29}$ is chosen from a hydrogen atom, $CH_3O$, $CH_3CH_2O$, and phenyl radicals, $R_{30}$ is chosen from a hydrogen atom and lower alkyl radicals, such as methyl and ethyl, $R_{31}$ is chosen from a hydrogen atom and lower alkyl radicals, such as methyl and ethyl, $R_{32}$ is chosen from lower alkyl radicals, such as methyl and ethyl, radicals of the formula: $-R_{33}-N(R_{31})_2$, wherein $R_{33}$ is chosen from $-CH_2-CH_2-$, $-CH_2-CH_2-_{CH2}-$, and $-CH_2-CH(CH_3)-$ groups, $R_{31}$ is chosen from a hydrogen atom and lower alkyl radicals, such as methyl and ethyl, and also the higher homologues of these radicals comprising up to 6 carbon atoms; and r is chosen such that the molecular weight ranges from 500 to 6 000 000, such as from 1000 to 1 000 000.

(8) amphoteric polymers of the type -D-X-D-X— chosen from:

a) polymers obtained by the action of chloroacetic acid and sodium chloroacetate on compounds comprising at least one monomeric unit of formula:

-D-X-D-X-D- (XVII)

wherein D is a radical

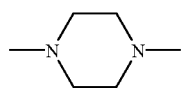

and X is chosen from the symbols E and E', wherein E and E', which may be identical or different, are chosen from divalent alkylene radicals with straight and branched chains comprising up to 7 carbon atoms in the main chain, wherein the divalent alkylene radicals are optionally substituted with at least one hydroxyl group. E or E' can additionally comprise at least one atom chosen from oxygen, nitrogen and sulphur atoms, and 1 to 3 aromatic and heterocyclic rings. The oxygen, nitrogen and sulphur atoms can be present in the form of at least one group chosen from ether, thioether, sulphoxide, sulphone, sulphonium, alkyl amine and alkenylamine groups, hydroxyl, benzyl amine, amine oxide, quaternary ammonium, amide, imide, alcohol, ester and urethane groups;

b) polymers of formula:

-D-X-D-X— (XVIII)

wherein D is a radical

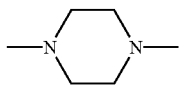

and X is chosen from the symbols E and E' and wherein at least one X is chosen from E'; E having the meaning given above and E' being chosen from alkylene divalent radicals with straight and branched chains comprising up to 7 carbon atoms in the main chain, which is optionally substituted with at least one hydroxyl radical and comprising at least one nitrogen atom substituted with an alkyl chain, which is optionally interrupted by an oxygen atom, and further comprising at least one functional group chosen from carboxyl functional groups and hydroxyl functional groups which are betainized by reaction with a reactant chosen from chloroacetic acid and sodium chloroacetate.

(9) ($C_1$–$C_5$)alkyl vinyl ether/maleic anhydride copolymers partially modified by semiamidation with at least one N,N-dialkylaminoalkylamine, such as N,N-dimethylaminopropylamine, or by semiesterification with at least one N,N-dialkanolamine. These copolymers may also comprise other vinyl comonomeric units such as vinylcaprolactam.

At least one amphoteric polymer may be chosen, for example, from polymers of family (1).

The at least one amphoteric polymer may be present in an amount ranging from 0.01% to 10% by weight, for example from 0.05% to 5% by weight, and further, for example, from 0.1% to 3% by weight, relative to the total weight of the composition.

In another new embodiment, a composition may comprise, for example, at least one surfactant.

The at least one surfactant may be chosen, for example, from anionic, amphoteric, non-ionic, zwitterionic and cationic surfactants, and mixtures thereof.

The at least one surfactant may be chosen, for example, from the following:

(i) Anionic Surfactant(s):

At least one anionic surfactant may be chosen, for example, from salts (for example, alkali metal salts, such as sodium salts, ammonium salts, amine salts, amino alcohol salts and magnesium salts) of the following compounds: alkyl sulphates, alkyl ether sulphates, alkylamino ether sulphates, alkylarylpolyether sulphates, monoglyceride sulphates; alkyl sulphonates, alkyl phosphates, alkyl amide sulphonates, alkyl aryl sulphonates, α-olefin sulphonates, paraffin sulphonates; ($C_6$–$C_{24}$)alkyl sulphosuccinates, ($C_6$–$C_{24}$)alkyl ether sulphosuccinates, ($C_6$–$C_{24}$)alkyl amide sulphosuccinates; ($C_6$–$C_{24}$)alkyl sulphoacetates; ($C_6$–$C_{24}$) acryl sarcosinates; and ($C_6$–$C_{24}$)acryl glutamates. At least one anionic surfactant may also be chosen, for example, from ($C_6$–$C_{24}$)alkylpolyglycoside carboxylic esters, such as alkylglucoside citrates, alkylpolyglycoside tartrates and alkylpolyglycoside sulphosuccinates, alkylsulphosuccinamates; acyl isethionates and N-acyl taurates, alkyl radicals and acyl radicals of these different compounds, such as those comprising from 12 to 20 carbon atoms, and at least one aryl radical may be chosen, for example, from phenyl and benzyl groups. At least one anionic surfactant may be chosen, for example, from fatty acid salts, such as oleic, ricinoleic, palmitic and stearic acid salts, coconut oil acid and hydrogenated coconut oil acid; acyl lactylates wherein the acyl radical comprises 8 to 20 carbon atoms. At least one anionic surfactant may be chosen, for example, from alkyl D-galactoside uronic acids and their salts, polyoxyalkylenated ($C_6$–$C_{24}$)alkyl ether carboxylic acids, polyoxyalkylenated ($C_6$–$C_{24}$)alkyl aryl ether carboxylic acids, polyoxyalkylenated ($C_6$–$C_{24}$)alkylamido ether carboxylic acids and their salts, for example, those comprising from 2 to 50 alkylene oxide groups, such as ethylene oxide groups, and mixtures thereof.

(ii) Non-Ionic Surfactant(s):

The at least one non-ionic surfactant may be chosen, for example, from compounds that are well-known (see "Handbook of Surfactants" by M. R. Porter, published by Blackie & Son (Glasgow and London), 1991, pp. 116–178). The at least one non-ionic surfactants may be chosen, for example, from polyethoxylated and polypropoxylated, alkyl phenols, alpha-diols and alcohols, comprising fatty chains comprising, for example, from 8 to 18 carbon atoms, and the number of ethylene oxide and propylene oxide groups may range from 2 to 50. The at least one non-ionic surfactant may be chosen, for example, from copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising on average 1 to 5, and, for example, 1.5 to 4, glycerol groups; polyethoxylated fatty amines comprising, for example, from 2 to 30 mol of ethylene oxide; oxyethylenated fatty acid esters of sorbitan comprising, for example, from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$–$C_{14}$) alkyl amine oxides and N-acylaminopropylmorpholine oxides.

(iii) Amphoteric or Zwitterionic Surfactant(s):

The at least one amphoteric or zwitterionic surfactant may be chosen, for example, from aliphatic secondary and tertiary amine derivatives wherein the aliphatic radical comprises linear and branched chains comprising 8 to 18 carbon atoms and comprising at least one water-solubilizing anionic group (for example, carboxylate, sulphonate, sulphate, phosphate and phosphonate); and ($C_8$–$C_{20}$)alkylbetaines, sulphobetaines, ($C_8$–$C_{20}$)alkylamido($C_1$–$C_6$)alkylbetaines and ($C_8$–$C_{20}$)alkylamido($C_1$–$C_6$)alkylsulphobetaines.

At least one amine derivative may be chosen, for example, from the products sold under the name Miranol, described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

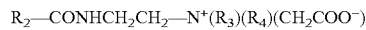

$R_2$—CONHCH$_2$CH$_2$—N$^+$(R$_3$)(R$_4$)(CH$_2$COO$^-$)

wherein: $R_2$ is chosen from alkyl radicals of acids $R_2$—COOH present in hydrolysed coconut oil, heptyl, nonyl and undecyl radicals, $R_3$ is chosen from beta-hydroxyethyl groups and $R_4$ is chosen from carboxymethyl groups; and

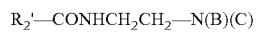

$R_2'$—CONHCH$_2$CH$_2$—N(B)(C)

wherein:

B is chosen from —CH$_2$CH$_2$OX', C is chosen from —(CH$_2$)$_z$—Y', wherein z=1 or 2, X' is chosen from the —CH$_2$CH$_2$—COOH group and a hydrogen atom, Y' is chosen from —COOH and the —CH$_2$—CHOH—SO$_3$H radical, $R_2'$ is chosen from alkyl radicals of acids $R_9$—COOH present in coconut oil and in hydrolysed linseed oil, alkyl radicals, such as $C_7$, $C_9$, $C_{11}$ and $C_{13}$ alkyl radicals, $C_{17}$ alkyl radicals and its is to form, and unsaturated $C_{17}$ radicals.

These compounds are classified, for example, in the CTFA dictionary, 5th edition, 1993, under the names Disodium Cocoamphodiacetate, Disodium Lauroamphodiacetate, Disodium Caprylamphodiacetate, Disodium Caprylo-amphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

Mention may be made of the cocoamphodiacetate sold, for example, under the trade name Miranol® C2M concentrate by the company Rhodia Chimie.

(iv) Cationic Surfactant(s):

At least one cationic surfactant may be chosen, for example, from: salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

The at least one cationic surfactant may be present in an amount ranging from 0.01% to 40%, such as from 0.5% to 30%, relative to the total weight of the composition.

A person of ordinary skill in the art will take care to select optional additional compound(s), such that at least one of the advantageous properties intrinsically associated with the oxidizing composition is not, or is not substantially, adversely affected by the envisaged addition(s).

Another new embodiment is a process for the oxidation dyeing of keratin fibres, such as human hair, using a dye composition comprising, in a cosmetically acceptable medium, at least one oxidation dye and at least one oxidizing composition.

According to the process, at least one dye composition is applied to the fibres, the colour being developed at acidic, neutral or alkaline pH using an oxidizing composition, which may be applied, for example, simultaneously or sequentially, with or without intermediate rinsing.

In another new embodiment, at least one dye composition described above is contemporaneously mixed, at the time of use, with at least one oxidizing composition. The mixture obtained is then applied to the keratin fibres and left to act for a period ranging from 3 to 50 minutes, such as from 5 to 30 minutes, after which the fibres may be optionally rinsed, optionally washed with shampoo, optionally rinsed again and optionally dried.

Another new embodiment is a process for permanently reshaping keratin fibres, such as human hair, using an oxidizing composition.

The first step of the process comprises applying to the fibres a reducing composition. This application may be performed, for example, lock by lock or globally.

A reducing composition may comprise, for example, at least one reducing agent, which may be chosen, for example, from thioglycolic acid, cysteine, cysteamine, glyceryl thioglycolate, thiolactic acid, and salts of thiolactic and thioglycolic acids.

A step of placing the fibres under tension in a shape of the final shape desired for the hair (for example, curls) may be carried out, for example, by any means, such as mechanical means, that is suitable for keeping hair under tension, such as rollers and curlers.

The fibres may also be shaped, for example, without the aid of external means, such as with the fingers.

Before proceeding to the following optional rinsing step, the fibres may, for example, be left to stand for a few minutes, such as a range from five minutes to one hour, for example from 10 to 30 minutes, so as to give the reducing agent enough time to act correctly on the fibres. This waiting phase may be performed, for example, at a temperature ranging from 35° C. to 45° C., while, for example, protecting the hair with a hood.

In a second optional step of the process (step (ii)), the fibres are impregnated with the reducing composition and rinsed thoroughly with an aqueous composition.

In a third optional step (step (iii)), the oxidizing composition is applied to the rinsed fibres, with the aim of fixing the new shape given to the fibres.

As in the case of applying the reducing composition, the fibres onto which the oxidizing composition has been applied may be left in a standing or waiting phase lasting a few minutes, such as from 3 to 30 minutes, for example from 5 to 15 minutes.

If the fibres were held under tension by external means, this means (rollers, curlers or the like) may be removed, for example, from the hair before or after the fixing step.

In another optional step of the process (step (iv)), the fibres impregnated with the oxidizing composition are rinsed, for example, with water.

Fibres that may be easy to disentangle and, perhaps, are soft may be obtained. The fibres may also be wavy.

In another new embodiment, an oxidizing composition may also be used, for example, in a process for bleaching keratin fibres, such as human hair.

The bleaching process may comprise applying an oxidizing composition to the fibres. The composition may comprise, for example, aqueous hydrogen peroxide solution in alkaline medium after extemporaneous mixing. A second optional step of the bleaching process may be, for example, rinsing the fibres.

Illustrative, non-limiting examples follow.

EXAMPLE 1

The ready-to-use aqueous bleaching composition below was prepared (amounts expressed as grams of active material):

| | |
|---|---|
| 200 volumes hydrogen peroxide | 12 |
| Stabilizer | qs |
| Polydimethylsiloxane of formula (I), sold under the name Belsil ADM 652 ® by the company Wacker | 2 |
| pH agent | qs pH 4.7 |
| Water | qs 100 |

The above bleaching composition was applied to natural hair and left for 45 minutes under a hood, and then rinsed thoroughly with water. A uniform lightening of the head of hair, and soft, light and easy to disentangle hair in a very satisfactory cosmetic condition, were obtained.

EXAMPLE 2

The bleaching composition below was prepared (amounts expressed as grams of active material):

| | |
|---|---|
| Potassium persulphate | 35 |
| Sodium persulphate | 30 |
| Sodium metasilicate | 14 |
| Ammonium chloride | 5 |
| EDTA | 1 |

-continued

| | |
|---|---|
| Sodium dioctyl sulphosuccinate/sodium benzoate | 1 |
| Calcium stearate | 1 |
| Polydimethylsiloxane of formula (II), sold under the name Fluid WR 1300 ® by the company Wacker | 2 |
| Silica | 7 |

40 grams of the above anhydrous composition were mixed with 80 grams of the aqueous composition below (amounts expressed as grams of active material):

Aqueous Composition

| | | |
|---|---|---|
| Cetearyl alcohol/Ceteareth-30 | | 2.85 |
| Stabilizers | | 0.06 |
| Sequestering agent | | 0.15 |
| 200 volumes hydrogen peroxide | | 9 |
| Phosphoric acid | qs | pH 2 |
| Distilled water | qs | 100 |

A ready-to-use bleaching cream was obtained, which, when applied and left for 45 minutes under a hood, produced a uniform bleaching of natural dark hair, the hair being in a very satisfactory cosmetic condition, soft, light and easy to disentangle.

EXAMPLE 3

Permanent-Reshaping Composition

The reducing composition below was prepared (amounts expressed as grams of active material):

| | | |
|---|---|---|
| Thioglycolic acid | | 9.2 |
| Arginine | | 15 |
| Aqueous ammonia comprising 20% NH$_3$ | | 1.86 |
| Ammonium carbonate | | 4.5 |
| Cocoylamidopropylbetaine/glyceryl monolaurate (25/5) as an aqueous 30% solution | | 1.3 |
| Peptizer | | 0.8 |
| Isostearyl alcohol (Tego Alkanol 66 sold by the company Goldschmidt) | | 12 |
| Sequestering agent | | 0.4 |
| Fragrance | | 0.4 |
| Demineralised water | qs | 100 |

This reducing composition was applied to a lock of wet hair, rolled up beforehand on a curler 9 mm in diameter.

After leaving the composition to act for ten minutes, the lock was rinsed thoroughly water.

The oxidizing composition below was then applied:

Oxidizing Composition:

(amounts expressed as grams of active material):

| | | |
|---|---|---|
| Polydimethylsiloxane of formula (II), sold under the name SLM 28020 ® by the company Wacker | | 2 |
| Aqueous hydrogen peroxide solution | | 8 volumes |
| Tetra sodium pyrophosphate (0.02 g) and sodium stannate (0.04 g) | | |
| Sequestering agent: pentasodium pentaacetate | | 0.06 |
| Demineralised water | qs | 100 |

After leaving the composition to act for ten minutes, the lock was rinsed thoroughly with water. The hair was then unrolled from the roller and dried.

The lock was wavy, with a very good cosmetic condition.

What is claimed:

1. A cosmetic composition for treating keratin fibres comprising, in a cosmetically acceptable medium:
   (i) at least one oxidizing agent, and
   (ii) at least one aminosilicone chosen from formulae (I) and (II):

$$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\left[\underset{\underset{(CH_2)_3}{|}}{\overset{\overset{R_2}{|}}{Si}}-O\right]_m-\underset{\underset{CH_3}{|}}{\overset{\overset{CH_3}{|}}{Si}}-R_3 \quad (I)$$

with $NH-(CH_2)_2-NH_2$ on the $(CH_2)_3$ branch wherein:
m and n are numbers with a sum (n+m) ranging from 1 to 1000,
n is a number ranging from 0 to 999, and m is a number ranging from 1 to 1000; and
$R_1$, $R_2$ and $R_3$, which may be identical or different, are chosen from a hydroxyl radical and $C_1$–$C_4$ alkoxy radicals, at least one of the radicals $R_1$ to $R_3$ being an alkoxy radical; and $$R_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_p-\left[\underset{\underset{(CH_2)_3}{|}}{\overset{\overset{CH_3}{|}}{Si}}-O\right]_q-\underset{\underset{CH_3}{|}}{\overset{\overset{CH_3}{|}}{Si}}-R_2 \quad (II)$$

with $NH-(CH_2)_2-NH_2$ on the $(CH_2)_3$ branch wherein:
p and q are numbers with a sum (p+q) ranging from 1 to 1000,
p is a number ranging from 0 to 999, and q is a number ranging from 1 to 1000; and $R_1$ and
$R_2$, which are different, are chosen from a hydroxyl radical and $C_1$–$C_4$ alkoxy radicals, at least one of the radicals $R_1$ and $R_2$ being an alkoxy radical.

2. The composition according to claim 1, wherein the keratin fibres are hair.

3. The composition according to claim 1, wherein the sum (m+n) ranges from 50 to 250.

4. The composition according to claim 1, wherein the sum (m+n) ranges from 100 to 200.

5. The composition according to claim 1, wherein n ranges from 49 to 249.

6. The composition according to claim 1, wherein n ranges from 125 to 175.

7. The composition according to claim 1, wherein m ranges from 1 to 10.

8. The composition according to claim 1, wherein m ranges from 1 to 5.

9. The composition according to claim 1, wherein the sum (p+q) ranges from 50 to 350.

10. The composition according to claim 1, wherein the sum (p+q) ranges from 150 to 250.

11. The composition according to claim 1, wherein p ranges from 49 to 349.

12. The composition according to claim 1, wherein p ranges from 159 to 239.

13. The composition according to claim 1, wherein q ranges from 1 to 10.

14. The composition according to claim 1, wherein q ranges from 1 to 5.

15. The composition according to claim 1, wherein the $C_1$–$C_4$ alkoxy radical is a methoxy radical.

16. The composition according to claim 1, wherein the at least one aminosilicone is chosen from formula (I) and has a hydroxyl/alkoxy molar ratio ranging from 0.2:1 to 0.4:1.

17. The composition according to claim 1, wherein the at least one aminosilicone is chosen from formula (I) and has a hydroxyl/alkoxy molar ratio ranging from 0.25:1 to 0.35:1.

18. The composition according to claim 1, wherein the at least one aminosilicone is chosen from formula (I) and has a hydroxyl/alkoxy molar ratio of 0.3.

19. The composition according to claim 1, wherein the at least one aminosilicone is chosen from formula (II) and has a hydroxyl/alkoxy molar ratio ranging from 1:0.8 to 1:1.1.

20. The composition according to claim 1, wherein the at least one aminosilicone is chosen from formula (II) and has a hydroxyl/alkoxy molar ratio ranging from 1:0.9 to 1:1.

21. The composition according to claim 1, wherein the at least one aminosilicone is chosen from formula (II) and has a hydroxyl/alkoxy molar ratio of 1:0.95.

22. The composition according to claim 1, wherein the at least one aminosilicone is chosen from formula (I) and has a weight-average molecular mass ranging from 2000 to 1 000 000.

23. The composition according to claim 1, wherein the at least one aminosilicone is chosen from formula (I) and has a weight-average molecular mass ranging from 3500 to 200 000.

24. The composition according to claim 1, wherein the at least one aminosilicone is chosen from formula (II) and has a weight-average molecular mass ranging from 2000 to 200 000.

25. The composition according to claim 1, wherein the at least one aminosilicone is chosen from formula (II) and has a weight-average molecular mass ranging from 5000 to 100 000.

26. The composition according to claim 1, wherein the at least one aminosilicone is chosen from formula (II) and has a weight-average molecular mass ranging from 10 000 to 50 000.

27. The composition according to claim 1, wherein the at least one aminosilicone is in the form of an oil-in-water emulsion and further comprises at least one surfactant.

28. The composition according to claim 27, wherein the at least one surfactant is chosen from cationic and non-ionic surfactants.

29. The composition according to claim 27, wherein the particle size of the at least one aminosilicone in the emulsion ranges from 3 to 500 nanometres.

30. The composition according to claim 29, wherein the particle size of the at least one aminosilicone in the emulsion ranges from 5 to 60 nanometres.

31. The composition according to claim 29, wherein the particle size of the at least one aminosilicone in the emulsion ranges from 10 to 50 nanometres.

32. The composition according to claim 1, wherein the at least one aminosilicone is chosen such that the contact angle with water of hair treated with a composition comprising 2% AM (active materials) of the at least one aminosilicone ranges from 90 to 180°.

33. The composition according to claim 32, wherein the contact angle with water of a hair treated with a composition containing 2% AM (active materials) of the at least one aminosilicone ranges from 90 to 130°.

34. The composition according to claim 1, wherein the composition comprising at least one aminosilicone is chosen such that the contact angle of a hair treated with said composition ranges from 90 to 180°.

35. The composition according to claim 34, wherein the at least one aminosilicone is present in an amount ranging from 0.01% to 20% by weight, relative to the total weight of the composition.

36. The composition according to claim 35, wherein the at least one aminosilicone is present in an amount ranging from 0.1% to 15% by weight, relative to the total weight of the composition.

37. The composition according to claim 36, wherein the at least one aminosilicone is present in an amount ranging from 0.5% to 10% by weight, relative to the total weight of the composition.

38. The composition according to claim 1, wherein the at least one oxidizing agent is chosen from hydrogen peroxide, urea peroxide, perborates, and persulphates.

39. The composition according to claim 38, wherein the at least one oxidizing agent is hydrogen peroxide.

40. The composition according to claim 39, wherein the hydrogen peroxide has a concentration ranging from 0.5 to 40 volumes.

41. The composition according to claim 40, wherein the hydrogen peroxide has a concentration ranging from 2 to 30 volumes.

42. The composition according to claim 40, wherein the hydrogen peroxide is in the form of an aqueous solution.

43. The composition according to claim 42, wherein the aqueous solution further comprises at least one stabilizer.

44. The composition according to claim 43, wherein the at least one stabilizer is chosen from alkali metal and alkaline-earth metal pyrophosphates; alkali metal and alkaline-earth metal stannates; phenacetin; and acid salts thereof and of oxyquinoline.

45. The composition according to claim 43, wherein the at least one stabilizer is chosen from stannates and stannates combined with pyrophosphates.

46. The composition according to claim 43, wherein the at least one stabilizer has a concentration ranging from 0.0001% to 5% by weight, relative to the total weight of the composition.

47. The composition according to claim 46, wherein the concentration ranges from 0.01% to 2% by weight, relative to the total weight of the composition.

48. The composition according to claim 43, wherein the ratio of the hydrogen peroxide to the at least one stabilizer ranges from 0.05:1 to 1000:1.

49. The composition according to claim 48, wherein the ratio of the hydrogen peroxide to the at least one stabilizer ranges from 0.1:1 to 500:1.

50. The composition according to claim 48, wherein the ratio of the hydrogen peroxide to the at least one stabilizer ranges from 1:1 to 200:1.

51. The composition according to claim 43, wherein the concentration ratio of the at least one aminosilicone to the at least one stabilizer ranges from 0.05:1 to 1000:1.

52. The composition according to claim 51, wherein the concentrations ratio of the at least one aminosilicone to the at least one stabilizer ranges from 0.1:1 to 500:1.

53. The composition according to claim 51, wherein the concentration ratio of the at least one aminosilicone to the at least one stabilizer ranges from 1:1 to 200:1.

54. The composition according to claim 1, wherein a concentration ratio of the at least one aminosilicone to the at least one oxidizing agent ranges from 0.001:1 to 10:1.

55. The composition according to claim 1, wherein the concentration ratio of the at least one aminosilicone to the at least one oxidizing agent ranges from 0.01:1 to 5:1.

56. The composition according to claim 1, wherein the concentration ratio of the at least one aminosilicone to the at least one oxidizing agent ranges from 0.02:1 to 1:1.

57. The composition according to claim 1, wherein the at least one oxidizing agent has a concentration ranging from 0.1% to 25% by weight, relative to the total weight of the composition.

58. The composition according to claim 1, wherein said composition is an aqueous solution having a pH ranging from 1 to 13.

59. The composition according to claim 58, wherein the pH ranges from 2 to 12.

* * * * *